(12) United States Patent
Mault

(10) Patent No.: US 6,482,158 B2
(45) Date of Patent: Nov. 19, 2002

(54) SYSTEM AND METHOD OF ULTRASONIC MAMMOGRAPHY

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 0 days.

(21) Appl. No.: 09/854,950

(22) Filed: May 14, 2001

(65) Prior Publication Data

US 2001/0044581 A1 Nov. 22, 2001

Related U.S. Application Data

(60) Provisional application No. 60/205,709, filed on May 19, 2000.

(51) Int. Cl.$^7$ ................................................. A61B 8/00
(52) U.S. Cl. ........................ 600/437; 600/443; 600/459; 128/915
(58) Field of Search ............................... 600/437, 442, 600/447, 459; 128/915–916

(56) References Cited

U.S. PATENT DOCUMENTS

| | | | |
|---|---|---|---|
| 2,630,798 A | 3/1953 | White et al. | 128/2.07 |
| 2,826,912 A | 3/1958 | Kritz | 73/194 |
| 2,831,348 A | 4/1958 | Kritz | 73/861.28 |
| 2,838,399 A | 6/1958 | Vogel, Jr. | 99/48 |
| 2,869,357 A | 11/1959 | Kritz | 73/32 |
| 2,911,825 A | 11/1959 | Kritz | 73/194 |
| 2,920,012 A | 1/1960 | Sanders et al. | 167/51.5 |
| 3,213,684 A | 10/1965 | Seaton et al. | 73/190 |
| 3,220,255 A | 11/1965 | Scranton et al. | 73/204 |
| 3,250,270 A | 5/1966 | Bloom | 128/2.07 |
| 3,306,283 A | 2/1967 | Arp | 128/2.07 |
| 3,523,529 A | 8/1970 | Kissen | 128/2.07 |
| 3,527,205 A | 9/1970 | Jones | 128/2.08 |
| 3,681,197 A | 8/1972 | Smith | 195/63 |
| 3,726,270 A | 4/1973 | Griffis et al. | 128/2.08 |

(List continued on next page.)

FOREIGN PATENT DOCUMENTS

| | | |
|---|---|---|
| DE | 198 10 476 | 9/1998 |
| EP | 0459647 A2 | 12/1991 |
| EP | 0 712 638 | 12/1995 |
| EP | 1013221 A1 | 6/2000 |
| GB | 2323292 | 9/1998 |
| WO | WO 96/40340 | 12/1996 |
| WO | 99/60925 | 5/1999 |

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise."

(List continued on next page.)

*Primary Examiner*—Francis J. Jaworski
(74) *Attorney, Agent, or Firm*—Gifford, Krass, Groh, Sprinkle, Anderson & Citkowski, P.C.

(57) ABSTRACT

A system for ultrasonic mammography includes an ultrasonic mammography device for constructing an ultrasonic image of a breast having a support structure with an ultrasonic transducer mounted on the support structure. The system also includes a personal digital assistant operatively connected to the ultrasonic transducer via a communication link, a patient computer system operatively connected to the personal digital assistant via a second communication link, and a healthcare provider computer system operatively connected to the patient computer system via an internet, for constructing the image of the breast. The method includes the steps of positioning the ultrasonic mammography device having an ultrasonic transducer on the patient and activating the ultrasonic transducer to generate a signal for constructing an image of the breast. The method also includes the steps of transmitting the signal from the ultrasonic transducer to the personal digital assistant, and transmitting the signal via an internet to a healthcare provider computer. The method further includes the steps of using the signal to construct an image of the patient's breast.

23 Claims, 3 Drawing Sheets

U.S. PATENT DOCUMENTS

| | | | |
|---|---|---|---|
| 3,797,480 A | 3/1974 | Williams | 128/2.08 |
| 3,799,149 A | 3/1974 | Rummel et al. | 128/2.07 |
| 3,814,091 A | 6/1974 | Henkin | 128/188 |
| 3,834,375 A | 9/1974 | Sanctuary et al. | 128/2.07 |
| 3,895,630 A | 7/1975 | Bachman | 128/2.07 |
| 3,938,551 A | 2/1976 | Henkin | 137/613 |
| 3,962,917 A | 6/1976 | Terada | 73/204 |
| 3,967,690 A | 7/1976 | Northcutt | 177/25 |
| 3,972,038 A | 7/1976 | Fletcher et al. | 340/189 M |
| 3,991,304 A | 11/1976 | Hillsman | 235/151.33 |
| 4,003,396 A | 1/1977 | Fleischmann | 137/83 |
| 4,008,712 A | 2/1977 | Nyboer | 128/2.1 Z |
| 4,051,847 A | 10/1977 | Henkin | 128/145.6 |
| 4,078,554 A | 3/1978 | Lemaitre et al. | 128/2.08 |
| 4,100,401 A | 7/1978 | Tutt et al. | 235/92 MT |
| 4,101,071 A | 7/1978 | Brejnik et al. | 235/92 MT |
| 4,113,039 A | 9/1978 | Ozaki et al. | 177/25 |
| 4,117,834 A | 10/1978 | McPartland et al. | 128/2 S |
| 4,151,668 A | 5/1979 | Hugerford | 40/495 |
| 4,159,416 A | 6/1979 | Brejnik et al. | 235/92 MT |
| 4,186,735 A | 2/1980 | Henneman et al. | 128/201.25 |
| 4,188,946 A | 2/1980 | Watson et al. | 128/204.22 |
| 4,192,000 A | 3/1980 | Lipsey | 364/415 |
| 4,197,857 A | 4/1980 | Osborn | 600/531 |
| 4,200,094 A | 4/1980 | Gedeon et al. | 128/201.13 |
| 4,211,239 A | 7/1980 | Raemer et al. | 128/716 |
| 4,212,079 A | 7/1980 | Segar et al. | 364/900 |
| 4,221,224 A | 9/1980 | Clark | 128/718 |
| 4,221,959 A | 9/1980 | Sessler | 377/13 |
| 4,224,952 A | 9/1980 | Sidorenko et al. | 128/782 |
| 4,230,108 A | 10/1980 | Young | |
| 4,244,020 A | 1/1981 | Ratcliff | 364/413 |
| 4,318,447 A | 3/1982 | Northcutt | 177/25 |
| 4,321,674 A | 3/1982 | Krames et al. | 364/413 |
| 4,341,867 A | 7/1982 | Johansen | 435/189 |
| 4,353,375 A | 10/1982 | Colburn et al. | 128/782 |
| 4,359,057 A | 11/1982 | Manzella | 128/718 |
| 4,366,873 A | 1/1983 | Levy et al. | 177/25 |
| 4,368,740 A | 1/1983 | Binder | 128/718 |
| 4,380,802 A | 4/1983 | Segar et al. | 364/900 |
| 4,386,604 A | 6/1983 | Hershey | 128/718 |
| 4,387,777 A | 6/1983 | Ash | 177/43 |
| 4,423,792 A | 1/1984 | Cowan | 177/25 |
| 4,425,805 A | 1/1984 | Ogura et al. | 73/861.29 |
| 4,440,177 A | 4/1984 | Anderson et al. | 600/532 |
| 4,444,201 A | 4/1984 | Itoh | 128/716 |
| 4,463,764 A | 8/1984 | Anderson et al. | 600/532 |
| 4,566,461 A | 1/1986 | Lubell et al. | 128/668 |
| 4,571,682 A | 2/1986 | Silverman et al. | 364/413 |
| 4,572,208 A | 2/1986 | Cutler et al. | 128/718 |
| 4,575,804 A | 3/1986 | Ratcliff | 364/715 |
| 4,577,710 A | 3/1986 | Ruzumna | 177/245 |
| 4,598,700 A | 7/1986 | Tamm | 128/671 |
| 4,608,995 A | 9/1986 | Linnarsson et al. | 128/713 |
| 4,619,269 A | 10/1986 | Cutler et al. | 128/719 |
| 4,629,015 A | 12/1986 | Fried et al. | 177/25 |
| 4,648,396 A | 3/1987 | Raemer | 600/534 |
| 4,650,218 A | 3/1987 | Hawke | 283/67 |
| 4,658,832 A | 4/1987 | Brugnoli | 600/532 |
| 4,686,624 A | 8/1987 | Blum et al. | 364/415 |
| 4,709,331 A | 11/1987 | Barkett et al. | 364/413 |
| 4,731,726 A | 3/1988 | Allen, III | 364/416 |
| 4,753,245 A | 6/1988 | Gedeon | 128/718 |
| 4,756,670 A | 7/1988 | Arai | 417/43 |
| 4,757,453 A | 7/1988 | Nasiff | 364/415 |
| 4,781,184 A | 11/1988 | Fife | 128/205.12 |
| 4,793,362 A | 12/1988 | Tedner | 128/734 |
| 4,796,182 A | 1/1989 | Duboff | 364/413.29 |
| 4,796,639 A | 1/1989 | Snow et al. | 600/532 |
| 4,803,625 A | 2/1989 | Fu et al. | 364/413.03 |
| 4,807,169 A | 2/1989 | Overbeck | 364/715.01 |
| 4,823,808 A | 4/1989 | Clegg et al. | 128/773 |
| 4,850,371 A | 7/1989 | Broadhurst et al. | 600/532 |
| 4,853,854 A | 8/1989 | Behar et al. | 364/413.01 |
| 4,855,942 A | 8/1989 | Bianco | 364/561 |
| 4,855,945 A | 8/1989 | Sakai | 364/709.2 |
| 4,856,531 A | 8/1989 | Merilainen | 600/532 |
| 4,880,014 A | 11/1989 | Zarowitz et al. | 128/734 |
| 4,891,756 A | 1/1990 | Williams, III | 364/413.29 |
| 4,894,793 A | 1/1990 | Ikemoto et al. | 364/709.03 |
| 4,895,163 A | 1/1990 | Libke et al. | 128/734 |
| 4,909,259 A | 3/1990 | Tehrani | 600/531 |
| 4,911,175 A | 3/1990 | Shizgal | 128/734 |
| 4,911,256 A | 3/1990 | Attikiouzel | 177/25.16 |
| 4,914,959 A | 4/1990 | Mylvaganam et al. | 73/861.28 |
| 4,917,108 A | 4/1990 | Mault | 600/531 |
| 4,924,389 A | 5/1990 | Gerbaulet et al. | 364/413.29 |
| 4,947,862 A | 8/1990 | Kelly | 128/734 |
| 4,951,197 A | 8/1990 | Mellinger | 364/413.2 |
| 4,954,954 A | 9/1990 | Madsen et al. | 364/413.29 |
| 4,955,946 A | 9/1990 | Mount et al. | 600/532 |
| 4,965,553 A | 10/1990 | DelBiondo, II et al. | 340/573 |
| 4,966,155 A | 10/1990 | Jackson | 128/671 |
| 4,986,268 A | 1/1991 | Tehrani | 128/204 |
| 4,998,018 A | 3/1991 | Kurahashi et al. | 250/343 |
| 5,007,429 A | 4/1991 | Treatch et al. | 128/677 |
| 5,012,411 A | 4/1991 | Policastro et al. | 364/413.06 |
| 5,019,974 A | 5/1991 | Beckers | 364/413.02 |
| 5,022,406 A | 6/1991 | Tomlinson | 128/719 |
| 5,033,561 A | 7/1991 | Hettinger | 177/25.16 |
| 5,038,773 A | 8/1991 | Norlien et al. | 128/205.23 |
| 5,038,792 A | 8/1991 | Mault | 128/718 |
| 5,042,500 A | 8/1991 | Norlien et al. | 600/532 |
| 5,042,501 A | 8/1991 | Kenny et al. | 600/532 |
| 5,060,506 A | 10/1991 | Douglas | 73/24.1 |
| 5,060,655 A | 10/1991 | Rudolph | 128/716 |
| 5,060,656 A | 10/1991 | Howard | 128/718 |
| 5,063,937 A | 11/1991 | Ezenwa et al. | 128/723 |
| 5,068,536 A | 11/1991 | Rosenthal | 250/341 |
| 5,069,220 A | 12/1991 | Casparie et al. | 128/719 |
| 5,072,737 A | 12/1991 | Goulding | 128/718 |
| 5,077,476 A | 12/1991 | Rosenthal | 250/341 |
| 5,081,871 A | 1/1992 | Glaser | 73/863.23 |
| 5,086,781 A | 2/1992 | Bookspan | 128/734 |
| 5,095,900 A | 3/1992 | Fertig et al. | 128/207.14 |
| 5,095,913 A | 3/1992 | Yelderman et al. | 128/719 |
| 5,117,674 A | 6/1992 | Howard | 73/31.07 |
| 5,119,825 A | 6/1992 | Huhn | 600/529 |
| 5,178,155 A | 1/1993 | Mault | 128/718 |
| 5,179,958 A | 1/1993 | Mault | 128/718 |
| 5,203,344 A | 4/1993 | Scheltinga | 128/734 |
| 5,214,966 A | 6/1993 | Delsing | 73/861.28 |
| 5,233,520 A | 8/1993 | Kretsch et al. | 364/413.29 |
| 5,233,996 A | 8/1993 | Coleman et al. | 600/529 |
| 5,263,491 A | 11/1993 | Thornton | 128/774 |
| 5,280,429 A | 1/1994 | Withers | 364/413.15 |
| 5,282,473 A | 2/1994 | Braig et al. | 600/532 |
| 5,282,840 A | 2/1994 | Hudrlik | 607/28 |
| 5,285,794 A | 2/1994 | Lynch | 128/719 |
| 5,293,875 A | 3/1994 | Stone | 128/719 |
| 5,299,579 A | 4/1994 | Gedeon et al. | 600/532 |
| 5,303,712 A | 4/1994 | Van Duren | 600/529 |
| 5,307,263 A | 4/1994 | Brown | 364/413.09 |
| 5,309,921 A | 5/1994 | Kisner et al. | 600/532 |
| 5,326,973 A | 7/1994 | Eckerbom et al. | 250/343 |
| 5,335,667 A | 8/1994 | Cha et al. | 128/34 |
| 5,355,879 A | 10/1994 | Brain | |
| 5,357,972 A | 10/1994 | Norlien | 128/725 |
| 5,363,857 A | 11/1994 | Howard | 600/531 |

| | | | |
|---|---|---|---|
| 5,372,141 A | 12/1994 | Gallup et al. ............... 128/734 |
| 5,387,164 A | 2/1995 | Brown, Jr. ................... 4829/9 |
| 5,388,043 A | 2/1995 | Hettinger ............... 364/413.29 |
| 5,398,688 A | 3/1995 | Laniado ................ 128/660.02 |
| 5,398,695 A | 3/1995 | Anderson et al. ........... 600/532 |
| 5,402,796 A | 4/1995 | Packer et al. .............. 128/719 |
| 5,412,560 A | 5/1995 | Dennison ............... 364/413.01 |
| 5,412,564 A | 5/1995 | Ecer ....................... 364/413.29 |
| 5,415,176 A | 5/1995 | Sato et al. ................. 128/734 |
| 5,417,222 A * | 5/1995 | Dempsey et al. ........... 128/903 |
| 5,419,326 A | 5/1995 | Harnoncourt .......... 128/660.02 |
| 5,421,344 A | 6/1995 | Popp ........................ 128/734 |
| 5,425,374 A | 6/1995 | Ueda et al. ................. 600/532 |
| 5,449,000 A | 9/1995 | Libke et al. ................ 128/734 |
| 5,450,193 A | 9/1995 | Carlsen et al. ............. 356/301 |
| 5,454,721 A | 10/1995 | Kuch ......................... 434/127 |
| 5,468,961 A | 11/1995 | Gradon et al. .............. 250/345 |
| 5,474,072 A * | 12/1995 | Shmulewitz ................ 128/915 |
| 5,485,402 A | 1/1996 | Smith et al. ................ 364/566 |
| 5,503,151 A | 4/1996 | Harnoncourt et al. .. 128/660.02 |
| 5,542,420 A | 8/1996 | Goldman et al. .......... 128/630 |
| 5,570,697 A | 11/1996 | Walker et al. ............. 128/719 |
| 5,579,782 A | 12/1996 | Masuo ....................... 128/734 |
| 5,611,351 A | 3/1997 | Sato et al. ................. 128/734 |
| 5,615,689 A | 4/1997 | Kotler ....................... 128/734 |
| 5,632,281 A | 5/1997 | Rayburn .................... 128/719 |
| 5,645,071 A | 7/1997 | Harnoncourt et al. ...... 128/719 |
| 5,647,370 A | 7/1997 | Harnoncourt ............... 128/725 |
| 5,673,691 A | 10/1997 | Abrams et al. ............. 128/630 |
| 5,676,132 A | 10/1997 | Tillotson et al. ....... 128/204.23 |
| 5,678,562 A | 10/1997 | Sellers ....................... 128/710 |
| 5,678,571 A | 10/1997 | Brown ....................... 128/898 |
| 5,691,927 A | 11/1997 | Gump .................. 364/709.01 |
| 5,704,350 A | 1/1998 | Williams, III ............... 128/630 |
| 5,705,735 A | 1/1998 | Acorn ......................... 73/23.3 |
| 5,720,296 A | 2/1998 | Cha ............................ 128/734 |
| 5,729,479 A | 3/1998 | Golan ..................... 364/709.2 |
| 5,740,801 A * | 4/1998 | Branson .................... 128/920 |
| 5,746,214 A | 5/1998 | Brown et al. ............... 128/693 |
| 5,754,288 A | 5/1998 | Yamamoto et al. ......... 356/301 |
| 5,788,643 A | 8/1998 | Feldman ..................... 600/506 |
| 5,789,660 A | 8/1998 | Kofoed et al. ............... 73/23.3 |
| 5,796,009 A | 8/1998 | Delsing .................. 73/861.28 |
| 5,796,640 A | 8/1998 | Sugarman et al. ..... 364/709.02 |
| 5,800,360 A | 9/1998 | Kisner et al. ............... 600/532 |
| 5,810,722 A | 9/1998 | Heikkila ..................... 600/300 |
| 5,816,246 A | 10/1998 | Mirza ......................... 128/726 |
| 5,817,031 A | 10/1998 | Masuo et al. ............... 600/547 |
| 5,819,735 A | 10/1998 | Mansfield et al. .......... 128/630 |
| 5,822,715 A | 10/1998 | Worthington et al. ......... 702/19 |
| 5,827,179 A | 10/1998 | Lichter et al. .............. 600/300 |
| 5,831,175 A | 11/1998 | Fletcher-Haynes ....... 73/861.28 |
| 5,832,448 A | 11/1998 | Brown ........................... 705/2 |
| 5,834,626 A | 11/1998 | DeCastro et al. ............ 73/23.3 |
| 5,836,300 A | 11/1998 | Mault ......................... 600/532 |
| 5,836,312 A | 11/1998 | Moore ....................... 128/897 |
| 5,876,351 A | 3/1999 | Rohde ........................ 600/523 |
| 5,890,128 A | 3/1999 | Diaz et al. ..................... 705/2 |
| 5,897,493 A | 4/1999 | Brown ....................... 600/300 |
| 5,899,855 A | 5/1999 | Brown ....................... 600/301 |
| 5,902,234 A | 5/1999 | Webb ......................... 600/300 |
| 5,908,301 A | 6/1999 | Lutz ........................... 434/236 |
| 5,910,107 A | 6/1999 | Iliff ............................ 600/300 |
| 5,913,310 A | 6/1999 | Brown ....................... 128/897 |
| 5,918,603 A | 7/1999 | Brown ....................... 128/897 |
| 5,922,610 A | 7/1999 | Alving et al. ............... 436/116 |
| 5,932,812 A | 8/1999 | Delsing .................. 73/861.02 |
| 5,933,136 A | 8/1999 | Brown ....................... 345/327 |
| 5,941,825 A | 8/1999 | Lang et al. ................. 600/449 |
| 5,951,300 A | 9/1999 | Brown ....................... 434/236 |
| 5,957,585 A | 9/1999 | Micheels et al. ........... 600/532 |
| 5,957,846 A * | 9/1999 | Chiang et al. .............. 600/447 |
| 5,974,124 A | 10/1999 | Schlueter, Jr. et al. .. 379/106.02 |
| 5,989,188 A | 11/1999 | Birkhoelzer et al. ........ 600/300 |
| 5,997,476 A | 12/1999 | Brown ....................... 600/300 |
| 6,010,459 A | 1/2000 | Silkoff et al. ............... 600/532 |
| 6,013,007 A | 1/2000 | Root et al. ...................... 482/8 |
| 6,014,578 A | 1/2000 | Minoz ........................ 600/350 |
| 6,015,389 A | 1/2000 | Brown ....................... 600/533 |
| 6,024,281 A | 2/2000 | Shepley ...................... 235/375 |
| 6,024,699 A | 2/2000 | Surwit et al. ............... 600/300 |
| 6,030,342 A | 2/2000 | Amano et al. .............. 600/301 |
| 6,032,676 A | 2/2000 | Moore ........................ 128/898 |
| 6,040,531 A | 3/2000 | Miller-Kovach et al. 177/25.16 |
| 6,042,383 A | 3/2000 | Herron ........................ 434/238 |
| 6,044,843 A | 4/2000 | O'Neil et al. ........... 128/204.23 |
| 6,045,513 A | 4/2000 | Stone et al. ................. 600/508 |
| 6,077,193 A | 6/2000 | Buhler et al. .................... 482/8 |
| 6,083,006 A | 7/2000 | Coffman ..................... 434/127 |
| 6,095,949 A | 8/2000 | Arai ............................... 482/4 |
| 6,095,985 A | 8/2000 | Raymond et al. ........... 600/513 |
| 6,101,478 A | 8/2000 | Brown ........................... 705/2 |
| 6,122,536 A | 9/2000 | Sun et al. .................... 600/341 |
| 6,135,950 A | 10/2000 | Adams ....................... 600/300 |
| 6,135,951 A | 10/2000 | Richardson et al. ........ 600/300 |
| 6,146,377 A * | 11/2000 | Lee et al. ...................... 606/13 |
| 6,283,761 B1 * | 9/2001 | Joao ........................... 434/236 |

OTHER PUBLICATIONS

British Journal of Anaesthesia, vol. 49, 1977 London (GB) pp. 575–587, J.A. Bushman et al. "Closed Circuit Anaesthesia."

Determination of Nitric Oxide Levels by Fluorescence Spectroscopy, Gabor G. and Allon, N. in Biochemical, Pharmacological, and Clinical Aspects of Nitric Oxide, edited by B.A. Weissman et al., Plenum Press, New York, 1995, p. 57.

IEEE Transactions on Biomedical Engineering, vol. 35, No. 9, Sep. 1988, pp. 653–659, Capek et al., "Noninvasive Measurement of Cardiac Output Using Partial CO2 Rebreathing."

Clinics in Chest Medicine (Review), vol. 10, 1989, pp. 255–264, Heigenhauser et al., "Measurement of Cardiac Output by Carbon Dioxide Rebreathing Methods."

* cited by examiner

SYSTEM AND METHOD OF ULTRASONIC MAMMOGRAPHY

RELATED APPLICATION

This application claims priority of United States Provisional Patent Application 60/205,709 filed May 19, 2000, and is incorporated herein by reference.

BACKGROUND OF THE INVENTION

1. Field of the Invention

The present invention relates generally to ultrasonic medical monitoring and, more specifically, to a system and method of ultrasonic mammography for detecting a physiological condition of a patient's breast.

2. Description of the Related Art

Medical monitoring involves the measurement of a physiological condition of a patient. An example of a medical monitor is disclosed in U.S. application Ser. No. 09/669,125 (filed Sep. 25, 2000) and Ser. No. 09/821,417 (filed Mar. 29, 2001, entitled "Monitoring System"), the disclosures of which are incorporated herein by reference. Conventional breast imaging is typically accomplished using a mammography ultrasound device within a medical setting, such as a hospital or clinic. The American Medical Association has set forth guidelines recommending how frequently a woman should undergo a mammography, since early detection of a medical condition, such as breast cancer, greatly affects the success of treatment for the condition. However, access to the hospital or clinic may affect the frequency in which the patient undergoes a mammography.

While the mammography devices currently used work well, some women may procrastinate in receiving a mammography, since the current method for obtaining an ultrasonic image of a breast typically often involves some discomfort to the patient, e.g. through pressing the breast as flat as possible. Thus, there is a need in the art for a system and method of breast imaging using ultrasonic measurements, which does not cause such discomfort. Further, the measurements may be carried out at the home of the user, and the information transmitted to a medical health provider over a communications network for analysis and evaluation purposes.

SUMMARY OF THE INVENTION

One advantage of the present invention is that a system and method of ultrasonic mammography is provided for remote imaging of a breast of a patient. Another advantage of the present invention is that a system and method is provided that obtains an ultrasonic image of the patient's breast, stores the data, and transmits the data to a healthcare provider via an Internet. Still another advantage of the present invention is that a system and method is provided that includes an ultrasonic transducer disposed within a brassiere device to obtain the ultrasonic image of the patient's breast. Yet still another advantage of the present invention is that a system and method is provided that includes a personal digital assistant that stores the measured data and transmits the data via the Internet to the healthcare provider. A further advantage of the present invention is that a system and method is provided wherein the healthcare provider can evaluate the image of the breast in real-time irrespective of the physical location of the patient and the healthcare provider. Yet a further advantage of the present invention is that a system and method is provided that is cost-effective in obtaining an image of the patient's breast.

Accordingly, the present invention is a system and method for ultrasonic mammography. The system for ultrasonic mammography includes an ultrasonic mammography device for constructing an ultrasonic image of a breast having a support structure with an ultrasonic transducer mounted on the support structure. The system also includes a personal digital assistant operatively connected to the ultrasonic transducer via a communication link, a patient computer system operatively connected to the personal digital assistant via a second communication link, and a healthcare provider computer system operatively connected to the patient computer system via an internet, for constructing the image of the breast. The method includes the steps of positioning the ultrasonic mammography device having an ultrasonic transducer on the patient and activating the ultrasonic transducer to generate a signal for constructing an image of the breast. The method also includes the steps of transmitting the signal from the ultrasonic transducer to the personal digital assistant, and transmitting the signal via an internet to a healthcare provider computer. The method further includes the steps of using the signal to construct an image of the patient's breast.

Other features and advantages of the present invention will be readily appreciated, as the same becomes better understood after reading the subsequent description taken in conjunction with the accompanying drawings.

DESCRIPTION OF THE PREFERRED EMBODIMENT(S)

Figure 1:
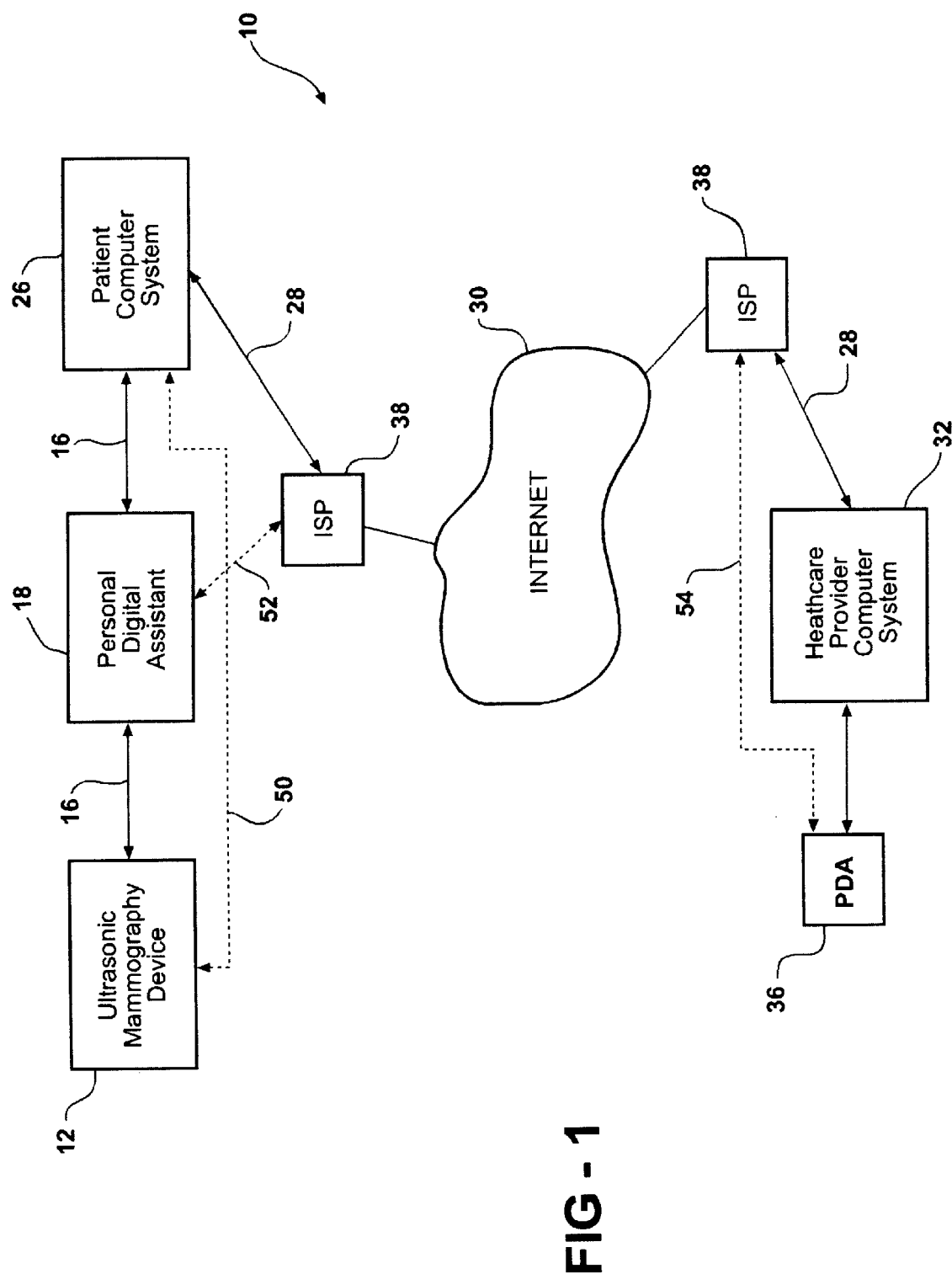
FIG. 1 is a schematic diagram of a system for ultrasonic mammography, according to the present invention.
Figure 2:
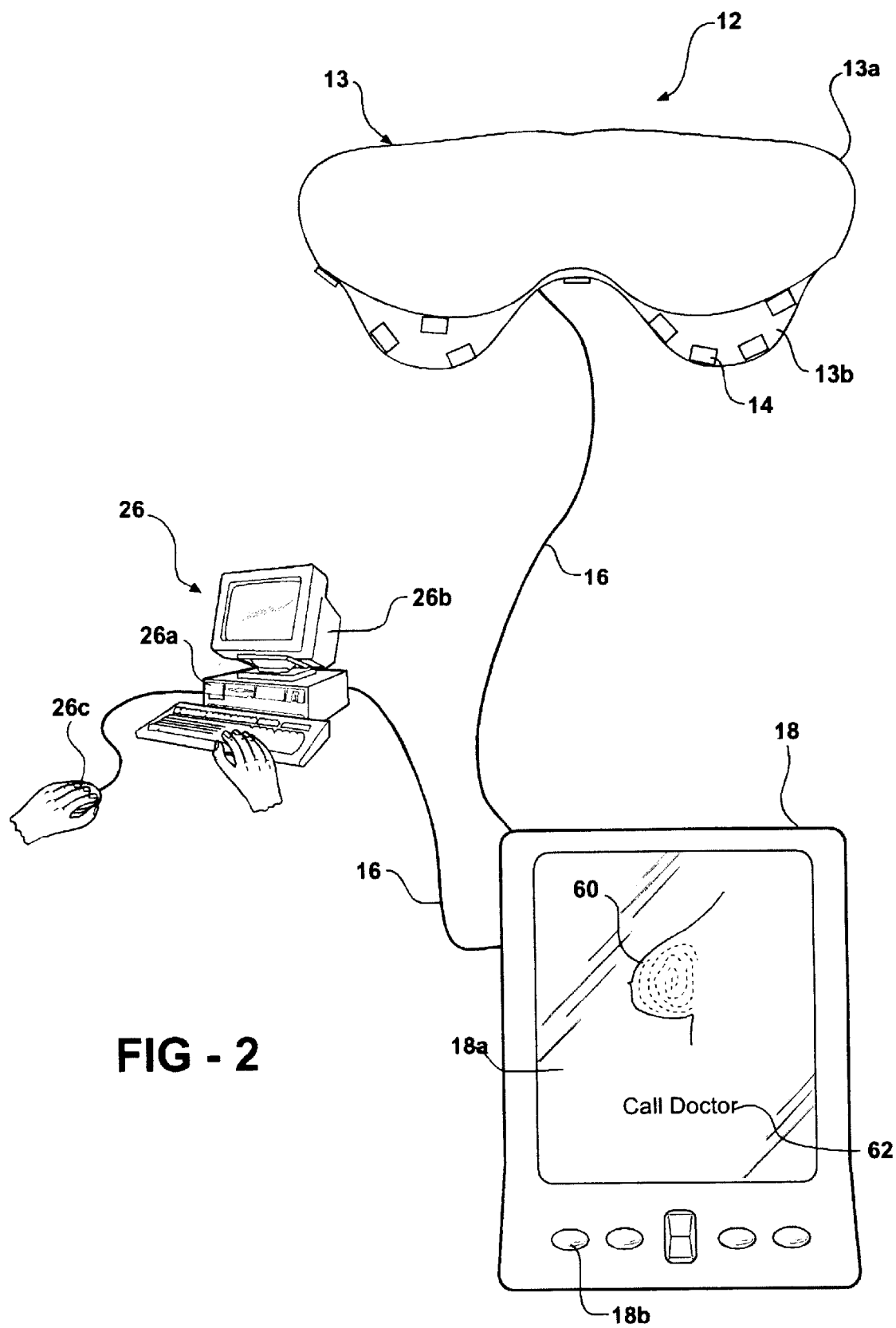
FIG. 2 is an elevational front view of an ultrasonic mammography device for the system of FIG. 1, according to the present invention.

Referring to FIG. 1 a system for ultrasonic mammography is illustrated. The system 10 includes an ultrasonic mammography device 12 having a brassiere shape. The device 12 is intended to be worn by a patient (not shown) to obtain an ultrasonic image of the patient's breast. The ultrasonic mammography device 12 includes a support structure 13 having a frame portion 13a and a cup portion 13b attached to the frame portion 13a. It should be appreciated that the frame portion 13a and cup portion 13b are integral and formed as one piece. Preferably, the size of the frame portion 13a and cup portion 13b is adjustable, to accommodate a variety of patient sizes. It should be appreciated that a uniform medium, such as water, other liquids, a gel, etc. may be used to take up volume in the cups 13b not filled by the patient's breasts.

The ultrasonic mammography device 12 also includes a predetermined number of ultrasonic transducers 14 arranged in a predetermined manner on the support structure, to construct the image of the breast. Each ultrasonic transducer 14 has a processor, a transmitter, and a receiver. The ultrasonic transducer 14 generates a signal, encapsulates the measurement data therein, and transmits the signal via a telecommunication link 16 to a personal digital assistant 18 in a manner to be described.

Ultrasonic transducers 14 of various types are suitable for this invention, e.g. devices containing piezoelectric crystals, conducting (e.g. metal) plates, micromachined semiconductors, etc. In the preferred embodiment, the transducers 14 are capable of both transmitting and detecting or receiving ultrasound. The active elements of the ultrasonic transducer 14 may be in direct contact with the patient's breast, or an intermediate layer (not shown), such as a gel or film. The gel is a conventional ultrasound coupling gel, or other such material, that prevents the formation of air voids when the ultrasonic transducer 14 is fitted to the patient, in order to reduce ultrasonic reflection from the skin surface of the patient. It should be appreciated that the gel can be applied either to the ultrasonic transducer 14 and/or skin of the patient, prior to placement of the ultrasonic mammography device 14 on the patient.

Activation of the ultrasonic transducer 14 generates an ultrasonic signal targeted at a predetermined fixed point, such as the breastbone of the patient. The ultrasonic signal bounces from the predetermined fixed point to the ultrasonic transducer 14, wherein the ultrasonic transducer 14 receives the ultrasonic signal. The processor portion of the ultrasonic transducer 14 calculates the distance of the ultrasonic path measured between the predetermined fixed point and the ultrasonic transducer 14.

Preferably, the ultrasonic transducer 14 is a microscopic transducer formed on a silicon wafer using an etching technique. A plurality of microscopic transducers may be arranged in a phased array. Ultrasonic sensors arrays such as those described in U.S. Pat. Nos. 5,894,452; 5,619,476; and 5,870,351, which are incorporated by reference, can be fabricated on silicon wafers using micromachining technology. It is known that such micromachined sensors may operate as either ultrasonic transmitters or detectors. An example of this type of a silicon-based ultrasonic transducer is manufactured by Sensant.

Data from each sensor array is collected and used to enhance the real-time image constructed from measurements made by the ultrasonic transducer 14. In another mode of operation, at least one sensor array is used as an ultrasound source while the other devices are used as imaging detectors. The roles of ultrasound source and imaging detectors are interchanged in various permutations, and a composite ultrasound image is generated by a computer. Alternatively, the ultrasonic transducer 14 includes two sensors attached at predetermined points surrounding the breast of the patient, and the path therebetween the sensors is measured.

Preferably, the predetermined number of ultrasonic transducers 14 are arranged in a predetermined manner around the front of the patient's body, and in particular the breast portion, but they may also be located around the side and back of the patient's body. For example, with four transducers 14, one transducer 14 operates as a detector, to detect a signal, such as ultrasound radiation transmitted from the second, third and fourth transducers. Likewise, when the second transducer 14 is operating as a detector, it receives the signal representing ultrasound radiation transmitted from the first, third or fourth transducers 14. It should be appreciated that for four transducers 14, there are 12 potential measurements, with different permutations of detector and receiver locations.

For example, a predetermined number of ultrasonic transducers 14 represented by N, requires N(N−1) such measurements. Assuming that ultrasound radiation detected by the first transducer 14 after transmission by the second transducer 14 carries the same information as that detected by the second transducer 14 after transmission by first transducer 14, the number of measurements may be reduced to (N/2)(N−1) without loss of information. However, this reduction may be at the expense of greater imaging errors. Preferably, the plurality of transducers 14 are arranged around the ultrasonic mammography device 12 in sufficient number in a manner to be described, to construct an ultrasonic image of the breast computationally from the measured data.

Hence, having a plurality of ultrasonic transducers 14 arranged around the ultrasonic mammography device 12 allows a large number of independent measurements to be made for use in constructing an image of the breast. For example, the measurements can be used to construct a three-dimensional ultrasonic image of the breast. The ultrasonic image of the breast allows for the visualization of tissue composing the breast and detection of conditions of the breast, such as a tumor. It should be appreciated that a two-dimensional image may also be constructed from the data. Another approach provides for the creation a database of detected intensity measurements for various receiver-transmitter pairs. Any significant changes in the database over time may indicate a condition such as formation of a tumor.

Preferably, the ultrasonic mammography device 12 is a rigid structure, that is fitted to the patient. The ultrasonic mammography device 12 can be allowed temporary flexibility during fitting to the patient. The relative positions of each of the ultrasonic transducers 14 on the support structure is determinable by measuring signal strengths for all transmitter-receiver permutations for the ultrasonic mammography device 12 in air, or in a uniform medium of known ultrasonic properties. If the overall transmission-receiver sensitivity is known for a particular receiver-transmitter pair, the signal strength is related to transmitter-receiver separation. If all transmitter-receiver distances are measured in this way, the relative spatial locations of the ultrasonic transducers 14 on the ultrasonic mammography device 12 is determinable. Transmitter-detector sensitivity is calibrated by independent measurements, e.g. forming the cup portion of the ultrasound mammography device 12 to a known shape.

In another embodiment, the ultrasound mammography device 12 is flexible, and is fitted to the breast of the patient before ultrasound measurements are taken of the breast. In this case, the relative positions of each of the ultrasonic transducers 14 may not be known accurately before ultrasound imaging begins, and imaging with absolute spatial accuracy may not be possible. However, a condition such as a tumor may be detected by identifying any localized regions of differing ultrasound absorption, for example by comparing the receiver outputs of closely spaced ultrasonic transducers 14. Computer modeling of the ultrasonic data provides a reasonable approximation of breast shape to create the ultrasonic images. For example, breast size or shape measurements can be determined by the patient at the time of ultrasonic imaging.

In operation, using N transducers 14, with one transducer 14 as a receiver, signals from the other N−1 receivers are detected. Alternatively, for a single transducer 14 used as a receiver, the signals are detected sequentially, allowing detected intensities for all transmitter-receiver pair combinations to be measured separately. In another example, signals from a plurality of transducers 14 may be detected simultaneously. In this case, the signals from different transducers 14 may be differentiated by different emission frequencies or different time-dependent modulations. Signal processing is used to differentiate the detected signals, and make relative intensity measurements for each of them. Data representing the ultrasound measurements is stored and processed in a manner to be described.

The system 10 includes a personal digital assistant (PDA) 18 having a memory, a processor, a display screen 18a and an input mechanism 18b that operatively receives the output signal generated by the ultrasonic transducer 14, processes the signal, and transmits the signal in a manner to be described. The PDA 18 includes all portable computing devices, such as a notebook computer, a hand-held computer, a palm-held organizer, a web-enabled cellular phone, or the like that provides computing and information storage and retrieval. In this example, the PDA 18 is a hand-held device, such as the Palm or Handspring Visor. It should be appreciated that in an alternative embodiment, a personal computer 24 (to be described) is used to receive, process and transmit the signal from the ultrasonic transducer 14, as shown at 50.

The system 10 also includes a telecommunication link 16 for communicating between the ultrasonic transducer 14 and the PDA 18. The telecommunication link 16 can be a wire operatively connecting the PDA and ultrasonic transducer. Alternatively, the telecommunication link is a wireless link. One example of a wireless link is a universal shortwave wireless connectivity protocol referred to as Bluetooth, as is known in the art. Another example of a wireless link is a memory module, also known as a memory stick. It should be appreciated that each ultrasonic transducer 14 transmits continuously at predetermined intervals based on a time unit contained therein, or at such a time as remotely triggered by a signal transmitted from the PDA 18.

The system 10 includes a patient computer system 26 operatively connected to the PDA 18, for receiving information from the PDA 18 and transmitting the information via a communication link 28 over the internet 30, to a healthcare provider computer system 32. The patient and healthcare provider computer systems 26, 32 are connected to an internet infrastructure 30, such as the Internet, via a telecommunication link 34, such as wires (e.g. a telephone line or a cable line) or a wireless connection. It should be appreciated that the patient computer system 26 and healthcare provider computer system 32 are conventional and known in the art. The patient computer system 26 includes a processor and memory 26a, display terminal 26b, and input device 26c.

In an alternative embodiment shown at 52, the PDA 18 is a wireless PDA capable of directly accessing the internet 30 using wireless technology, as is known in the art. It should be appreciated that the healthcare provider may access the patient information on the healthcare provider computer system 32. Alternatively, the healthcare provider can access the information via a PDA 36, as shown at 54.

As is known in the art, the Internet 30 includes providers, such as Internet Access Providers (IAPs), Internet Service Providers (ISPs) and Network Service Providers (NSPs) (not shown) and routers (not shown) that provide wired and wireless digital telecommunications throughout the world using a TCP/IP networking protocol. It should be appreciated that the computers 26, 32 or PDAs 18, 36 may access the Internet directly, or they may be operatively connected to a Local Area Network (LAN) (not shown) over which information is transmitted to other computers on the same LAN or to computers on other LANS through a localized Intranet.

The Internet 30 includes a plurality of web site servers (not shown) that interactively transfer information to a user through the user's computer. The web site server is a computer system operatively connected to a provider in a conventional manner. The web site provides for interactive communication between the host of the web site and a visitor to the web site. The communication is facilitated by a series of screens, referred to as pages, displayed on the display screen, with the first page referred to as a home page. When the user visits a particular web site, the user is served a page displayed on the video monitor referred to as a home page. The user may interact with the page via the input device, such as by making a selection or a request.

In the preferred embodiment, the ultrasound data from the ultrasound mammography device 12 is transferred to a personal digital assistant (PDA) or portable computer in the possession of the patient. Data transfer can use a wireless, IR, optical, other electromagnetic radiation, or electrical link. It should be appreciated that images may be computed by the PDA 18, or alternatively by the healthcare provider computer system 32. Data, and/or images are transmitted, preferably using a computer network such as the Internet, to a computer accessible by a physician or other healthcare professional. The physician can study the data or images, and make a diagnosis. A computer expert system resident with the healthcare provider computer system 32 can also be used to determine if there is a medical condition associated with the data or images.

Figure 3:
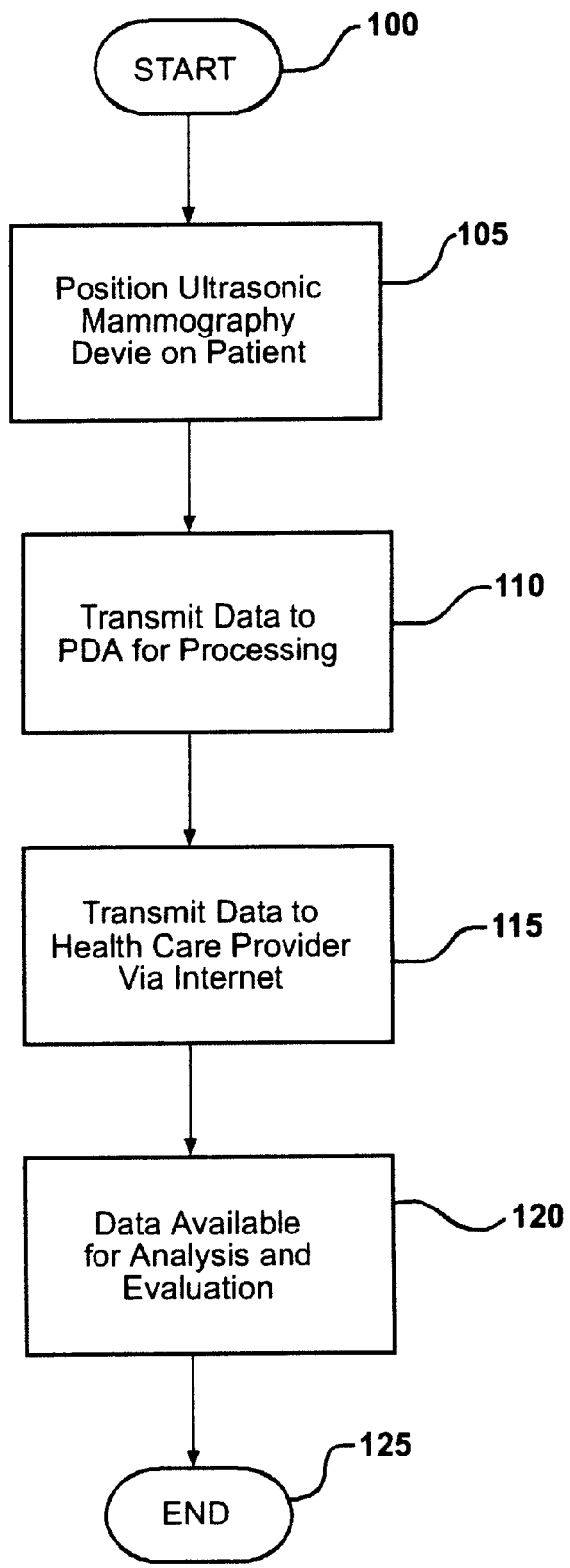
FIG. 3 is a flowchart of a method for ultrasonic mammography, according to the present invention, utilizing the system of FIG. 1.

Referring to FIG. 3, a method for ultrasonic mammography is provided. The method begins in bubble 100 and continues to block 105, with positioning the ultrasound mammography device 12 on the patient, so that the transducers 14 surround the breast, as previously described. The ultrasonic transducer 14 is activated, to generate an ultrasound radiation signal used in constructing a real-time three-dimensional image of the breast, as previously described. The methodology advances to block 110.

In block 110, the data in the form of a signal from the ultrasonic transducer 14 is transmitted to the PDA 18 for processing. The PDA 18 receives the data from the ultrasonic transducer 14 and generates a set of values and interpretive information from the data. The data is stored on the PDA 18. For example, the PDA 18 receives the data as a set of ultrasonic path measurements sampled during a predetermined time interval and a set of predetermined timestamps, wherein each measurement has a corresponding timestamp. The PDA 18 includes software which algorithmically evaluates the measurement values to construct the image of the breast.

Preferably, the processed data is displayed on the display screen 18a of the PDA 18 as an image as shown at 60. Advantageously, the processed data can be compared to a predetermined criterion, such as image quality, and a message is displayed on the display screen 18a. For example, the message may prompt the user to contact the healthcare provider, as shown at 62. The user of the PDA 18 reviews the screens, redisplays selected screens, or inputs data into displayed fields by utilizing the operator control devices of the PDA 18; e.g., a stylus. As one skilled in the art will recognize, the capabilities of the PDA 18 include the functionality to process and display the information as dictated by the objectives of the healthcare provider.

In an alternative embodiment, the PDA 18 transmits the data via the Internet 30 to the healthcare provider for processing. The data is processed and analyzed in the healthcare provider's computer system 32, to construct the image of the patient's breast.

The methodology advances to block 115, and the processed data is transmitted by the PDA 18 to the healthcare provider via the Internet 30, as previously described. The methodology advances to block 120.

In block 120, the data is received by the healthcare provider and made available to the healthcare provider for further analysis and study. For example, the data is stored on a database on the healthcare provider's computer system 32. The information is retrieved and displayed in the form of web pages. The server stores and displays the information via web pages, either by itself or in combination with previously stored information pertinent to a particular patient profile. Further, the server utilizes various software components to process and present the information according to predetermined care objectives. It should be appreciated that the server can process data from a plurality of patients.

The healthcare provider retrieves the information via a variety of means. Typically, the server displays the information on the web pages; however, the healthcare provider may download the information from the server to a computing device of his/her choice; e.g., a PDA 36 or another personal computer (not shown).

It should be appreciated that the healthcare provider can communicate with the patient on the PDA 18. For example, the healthcare provider, after reviewing the patient's information, uploads a text message from their computer to a common interface, such as the web site. The server of the web site transmits the information via the Internet 30 to the PDA 18, which activates an alarm to notify the patient of an incoming message, and displays the same on the display unit portion of the PDA 18 as shown at 62.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. An ultrasonic mammography device for constructing an image of a breast comprising:
   (a) a support structure having a brassiere shape that is worn by a patient;
   (b) at least one ultrasonic transmitter mounted on the support structure in a predetermined position; and
   (c) at least one ultrasonic detector mounted on the support structure in a predetermined position, wherein ultrasonic measurements from the ultrasonic transmitter and ultrasonic detector are used in constructing the image of the patient's breast.

2. The ultrasonic mammography device of claim 1, wherein the support structure includes a frame portion and a cup portion that are integral and formed as one piece.

3. The ultrasonic mammography device of claim 1, wherein the ultrasonic transmitter and ultrasonic detector are a silicon-based ultrasonic transducer.

4. A system for ultrasonic mammography comprising:
   an ultrasonic mammography device for constructing an ultrasonic image of a breast, wherein the ultrasonic mammography device includes a support structure having an ultrasonic transducer mounted on the support structure in a predetermined position for constructing an image of the breast;
   a personal digital assistant operatively connected to said ultrasonic transducer via a communication link;
   a patient computer system operatively connected to said personal digital assistant via a second communication link, wherein said patient computer system includes a memory, a processor, a display device and an input device; and
   a healthcare provider computer system operatively connected to said patient computer system via a communications network, wherein said healthcare provider computer system includes a memory, a processor, a display device and a input device and activation of said ultrasonic transducer generates a data signal that is transmitted to said personal digital assistant via said communication link, and transmission of said signal to said healthcare provider computer system via said second communication link, for constructing the image of the breast.

5. A system as set forth in claim 4 wherein said ultrasonic transducer is an ultrasonic transducer having a plurality of microscopic transducers arranged in an array on a silicon wafer.

6. A system as set forth in claim 4 wherein said PDA includes a memory, a processor, a display screen and an input mechanism.

7. A system as set forth in claim 4 wherein said communication link is a Bluetooth wireless communication link.

8. A system as set forth in claim 4 wherein the communications network is the Internet.

9. A system as set forth in claim 4 wherein said healthcare provider computer system is operatively connected to a plurality of patient computer systems, for evaluating a plurality of patients.

10. A system for ultrasonic mammography comprising:
    an ultrasonic mammography device having a predetermined number of ultrasonic transducers, with each having a processor, a transmitter and a receiver in a predetermined position, and each arranged wherein said ultrasound mammography device is positioned over the breast of the patient;
    a personal digital assistant operatively connected to said ultrasonic transducer via a communication link, wherein said personal digital assistant includes a memory, a processor, a display screen, an input mechanism, and a wireless communication mechanism for wireless communication via the internet;
    a healthcare provider computer system in communication with said personal digital assistant via a communications network, wherein said healthcare provider computer system includes a memory, a processor, a display device and an input device; and
    activation of said ultrasonic transducer generates transmission of a data signal to said personal digital assistant via said communication link, and wireless transmission of said signal between said personal digital assistant and said healthcare provider computer system over the communications network for analysis by the healthcare provider.

11. A system as set forth in claim 10 wherein said ultrasonic transducer is an ultrasonic transducer having a plurality of microscopic transducers arranged in an array on a silicon wafer.

12. A system as set forth in claim 10 wherein said communication link is a Bluetooth wireless communication link.

13. A system as set forth in claim 10 wherein the communications network is the Internet.

14. A system as set forth in claim 10 wherein said healthcare provider computer system is operatively connected to a plurality of patient computer systems for simultaneously evaluating a plurality of patients.

15. A system as set forth in claim 10 wherein said ultrasonic transducer is an ultrasonic transducer having a plurality of microscopic transducers arranged in an array on a silicon wafer.

16. A method of ultrasonic mammography, said method comprising the steps of:

positioning an ultrasonic mammography device having an ultrasonic transducer on the patient to obtain an image of the patient's breast;

activating the ultrasonic transducer to generate a signal, wherein the ultrasonic transducer includes a processor, a transmitter and a receiver;

transmitting the signal from the ultrasonic transducer to a personal digital assistant, wherein the personal digital assistant includes a memory, a processor, a display screen and an input mechanism;

transmitting the signal from the personal digital assistant via a communications network to a healthcare provider computer, wherein the healthcare provider computer includes a memory, a processor, a display screen and an input device; and using the signal to construct an image of the patient's breast.

17. A method as set forth in claim 16 wherein said ultrasonic transducer is an ultrasonic transducer having a plurality of microscopic transducers arranged in an array on a silicon wafer.

18. A method as set forth in claim 16 wherein said step of transmitting the signal between the ultrasonic transducer and the personal digital assistant includes transmitting the signal via a Bluetooth wireless communication link.

19. A method as set forth in claim 16 wherein said step of transmitting the signal from the personal digital assistant includes the step of transmitting the signal via the Internet.

20. A method as set forth in claim 16 wherein said step of transmitting the signal from the personal digital assistant includes the step of transmitting the signal to a patient computer system having a memory, a processor, a display screen, and an input device.

21. A system as set forth in claim 16 including the step of receiving, by said healthcare provider computer system, a plurality of signals from a plurality of patients, for simultaneously evaluating a plurality of patients.

22. A system as set forth in claim 16 wherein said step of using the signal includes the step of using the personal digital assistant to construct an image of the patient's breast from the signal.

23. A system as set forth in claim 16 wherein said step of using the signal includes the step of using the healthcare provider computer to construct an image of the patient's breast.

* * * * *